United States Patent [19]
Johnson, II

[11] Patent Number: 5,580,163
[45] Date of Patent: Dec. 3, 1996

[54] FOCUSING LIGHT SOURCE WITH FLEXIBLE MOUNT FOR MULTIPLE LIGHT-EMITTING ELEMENTS

[75] Inventor: Howard W. Johnson, II, Crystal, Minn.

[73] Assignee: August Technology Corporation, Edina, Minn.

[21] Appl. No.: 277,952

[22] Filed: Jul. 20, 1994

[51] Int. Cl.⁶ .................................................. F21V 19/02
[52] U.S. Cl. .......................... 362/285; 362/239; 362/240; 362/800
[58] Field of Search ................................. 362/285, 278, 362/320, 238, 250, 800, 804, 239, 240

[56] References Cited

U.S. PATENT DOCUMENTS

| | | | |
|---|---|---|---|
| 4,164,008 | 8/1979 | Miller et al. | 362/800 |
| 4,803,607 | 2/1989 | Jönsson | 362/238 |
| 5,063,248 | 7/1991 | McEwan et al. | 362/800 |
| 5,122,939 | 6/1992 | Kazdan et al. | 362/800 |
| 5,162,696 | 11/1992 | Goodrich | 362/800 |

Primary Examiner—Leonard E. Heyman
Attorney, Agent, or Firm—Sand & Sebolt

[57] ABSTRACT

A single flexible mount and a simple adjustment system are used to provide the means to focus the collective outputs of multiple light-emitting elements.

20 Claims, 4 Drawing Sheets

FOCUSING LIGHT SOURCE WITH FLEXIBLE MOUNT FOR MULTIPLE LIGHT-EMITTING ELEMENTS

BACKGROUND—FIELD OF INVENTION

This invention relates to illumination, specifically to a method of adjusting or focusing multiple illumination sources that improves performance and broadens applicability.

BACKGROUND—DESCRIPTION OF PRIOR ART

When using artificial illumination to view a given object, it is often necessary to have uniform light distribution over the entire field of view. Along with uniform distribution, the light is frequently required to come at the object from more than one angle in order to reduce the possibility of shadows. Both uniform light distribution and a reduction of shadowing can be achieved by illuminating with multiple light-emitting elements (light bulbs, LEDs(Light Emitting Diodes), fiber optic cables, etc.) placed at intervals near the object to be illuminated. Each element tends to eliminate the shadows that are the result of any other given element. Examples of Multiple Light-Emitting Element (MLEE) illumination sources include fiber optic ringlights (each fiber acts as a separate light emitting element), fluorescent ring lights (although not technically a MLEE illuminator, the fluorescent bulb emits light along its entire length, which approximates a series of point sources), and light sources that are composed of a series of incandescent bulbs, LEDs, or fiber optic cables. These illumination sources are used in a variety of scientific and non-scientific applications, and have been generally fixed or very limited in their ability to adjust or focus the direction of their light output. Without the ability to focus the illuminator the light intensity decreases dramatically as the distance to the illuminated object is increased. The inability to readily focus the direction of light output limits the performance and application of today's MLEE illuminators.

Attempts to provide adjustability or focusing of ring lights have relied on mechanical and generally expensive mechanisms. This fact has resulted in their limited use, confined to those applications that can justify the potential maintenance and expense.

FIG. 5 shows that prior art in the form of a fiber optic ringlight where each fiber optic illumination point is adjustable separate from the others by a screw.

SUMMARY

A focusing light source comprising: a flexible membrane to which a plurality of light emitting elements are afixed, a physical means of flexing this membrane so that the light from the collective outputs of the light emmitting elements can be focused over a range of working distances.

OBJECTS AND ADVANTAGES

Accordingly, the objects and advantages of my invention are the ability to readily adjust or focus multiple light-emitting elements using few moving parts while still offering ease of adjustment. Providing convenient re-direction of light output allows an illumination source to be rapidly optimized for a particular application or to be utilized in applications that were previously not feasible. It is a further object of this invention to have a higher reliability than previous mechanical focusing mechanisms because there are fewer parts to break down and wear out. Fewer moving mechanical contact surfaces produce fewer breakdown particles which is an advantage in certain industries (notably integrated circuit manufacturing and the medical device industry) where there is a need to keep particle contamination to a minimum. Another advantage of this invention is ease of manufacture. This is a result of the low parts count and the novelty of the flexible mount. Manufacturing costs are reduced minimizing market price barriers.

Still further objects and advantages will become apparent from a consideration of the ensuing description and accompanying drawings.

Figure 1:
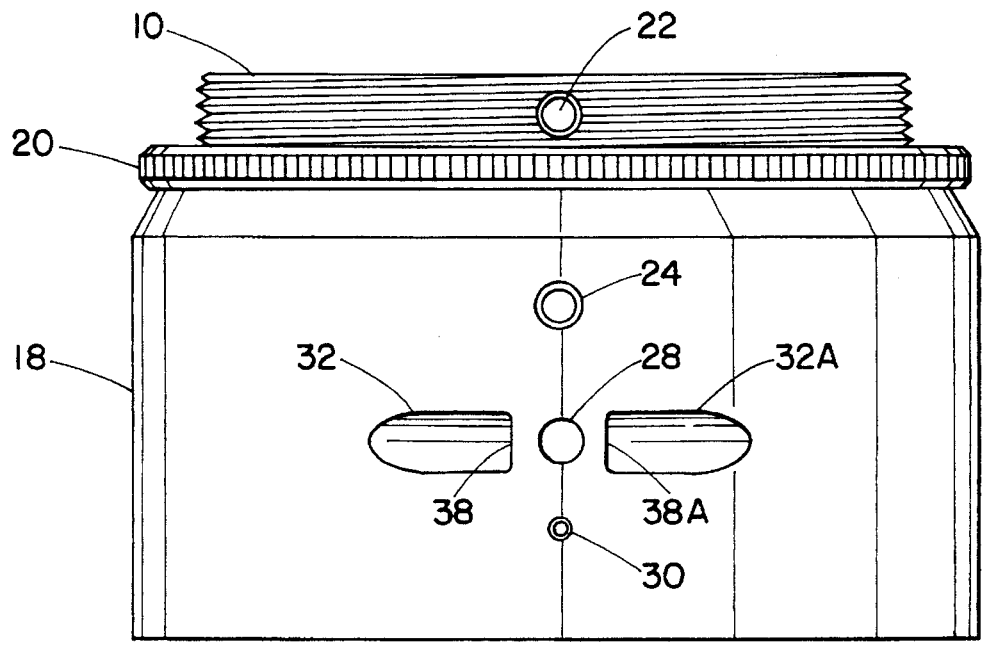
FIG. 1 shows an exterior view of the preferred embodiment.

REFERENCE NUMERALS 10 inside housing
16 flexible light-emitting clement mount
18 outside housing
20 focus adjustment ring
22 mounting screw
22A mounting screw
22B mounting screw
24 focus adjustment limit screw
26 focus adjustment lock screw
28 cable through hole
30 outer ring retaining screw
30A outer ring retaining screw
30B outer ring retaining screw
32 cable retaining screw relief cut
32A cable retaining screw relief cut
34 light-emitting element
34A light-emitting element
34B light-emitting element
34C light-emitting element
34D light-emitting element
34E light-emitting element
34F light-emitting element
34G light-emitting element
34H light-emitting element
34I light-emitting element
34J light-emitting element
34K light-emitting element 34L light-emitting element
34M light-emitting element
34N light-emitting element
34O light-emitting element
34P light-emitting element
34Q light-emitting element
36 mount outer ring
38 cable retaining screw
38A cable retaining screw
42 focus adjustment limit slot

PREFERRED EMBODIMENT—DESCRIPTION

FIG. 1. Exterior View of Preferred Embodiment

FIG. 1 shows a view of the exterior of the preferred embodiment of the present invention. The device comprises an outside housing 18 (FIG. 1) which is cylindrical and encloses the majority of an inside housing 10 (FIG. 1) which is also cylindrical. The lower portions of outside housing 18 and inside housing 10 (FIG. 2 cross-section) are connected by a flexible light-emitting element mount 16 and by a mount outer ring 36. The upper portion of inside housing 10 is threaded on its outside diameter and protrudes through a focus adjustment ring 20 (FIG. 2) which has female threads on its inside diameter. The male (external) threads on inside housing 10 mate with the female (internal) threads on focus adjustment ring 20. The outside diameter of focus adjustment ring 20 is sufficiently large to prohibit its entry into the upper interior bore diameter of outside housing 18. Set at the same distance from the upper edge of inside housing 10 there is a mounting screw 22 (FIG. 1), a mounting screw 22A, and a mounting screw 22B. Mounting screws 22, 22A, and 22B are each 120 degrees apart. A focus adjustment limit slot 42 (FIG. 2) is incorporated into the outside diameter of inside housing 10. Focus adjustment limit slot 42 houses the end of a focus adjustment limit screw 24 which is threaded into the wall of outside housing 18 (FIG. 1 and FIG 2).

Figure 4:
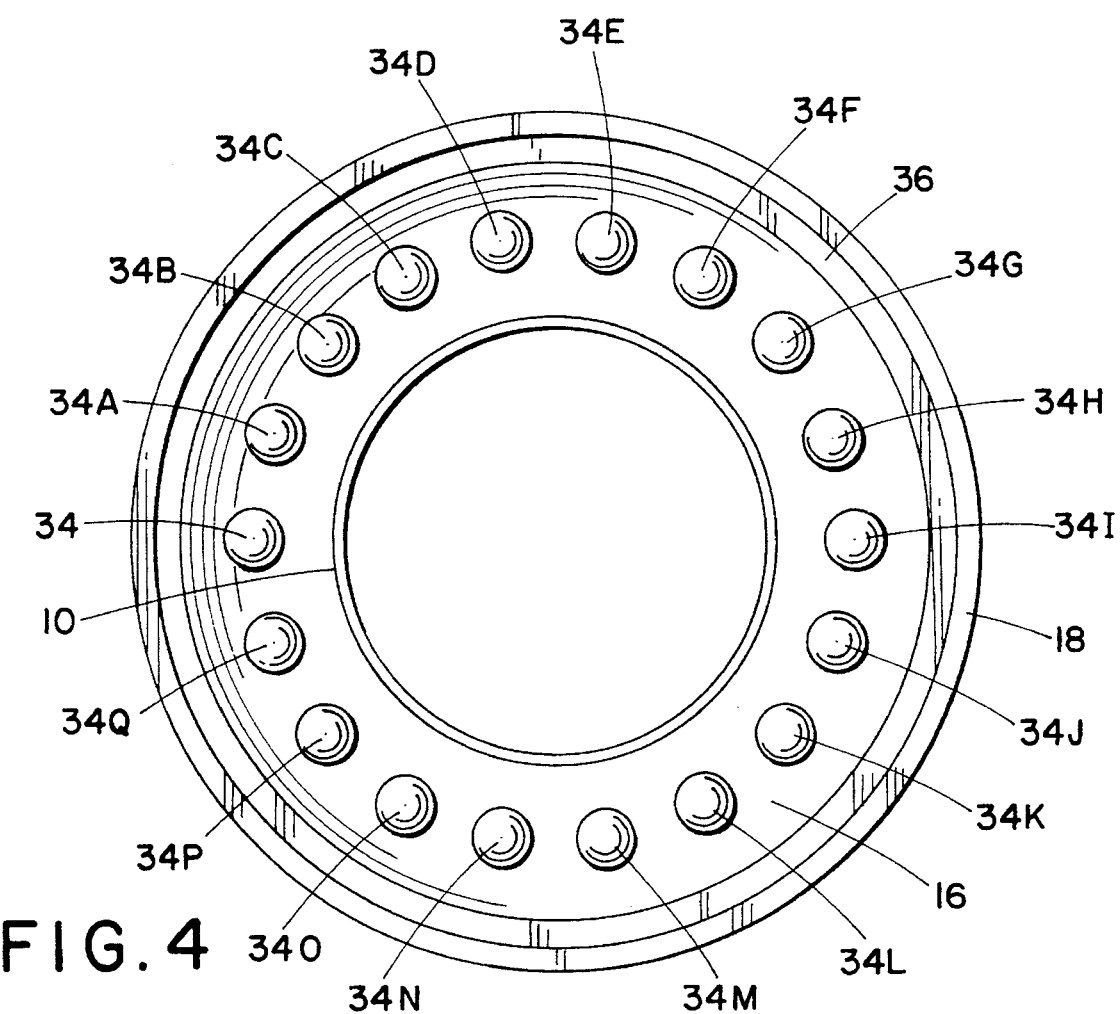
FIG. 4 is a view of the underside of the embodiment displayed in FIG. 1.
Figure 2:
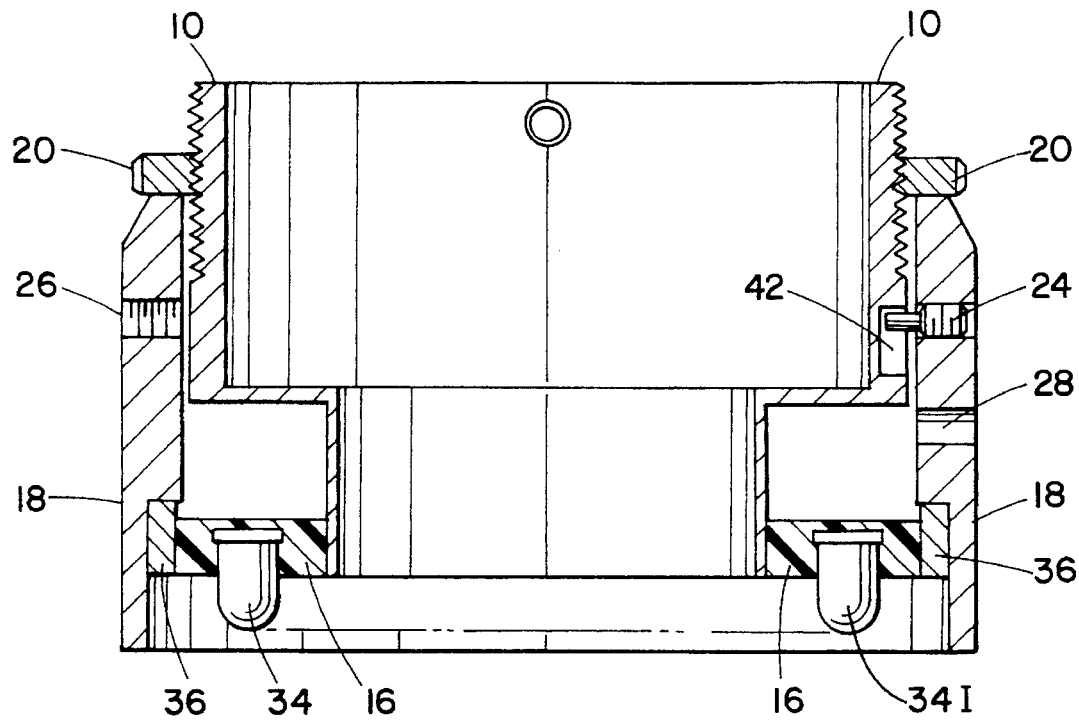
FIG. 2 shows a cross section of the invention with the flexible light-emitting element mount in the nominal position.

Opposite screw 24 on outside housing 18 is a focus adjustment lock screw 26 (FIG. 2). The lower portion of inside housing 10 is of a reduced diameter and has been coated on its outside diameter with a prime coat to insure that the inside diameter of flexible light-emitting element mount 16 (FIG. 2) will adhere to its circumference when flexible mount 16 is molded in place. Mount outer ring 36 is secured in a recess on the inside of outer housing 18 by outer ring retaining screw 30 (FIG. 1), by outer ring retaining screw 30A, and by outer ring retaining screw 30B which are all 120 degrees apart. The inside diameter of mount ring 36 (FIG. 2) is also coated with prime coat so that the outside diameter of flexible mount 16 (FIG. 2) will adhere to it during molding. The flexible mount 16 is cast from high strength mold making silicone or any suitable flexible material. Also adhered to during the molding process are a light-emitting element 34, a light-emitting element 34A, a light-emitting element 34B, a light-emitting element 34C, a light-emitting element 34D, a light-emitting element 34E, a light-emitting element 34F, a light-emitting element 34G, a light-emitting element 34H, a light-emitting element 34I, a light-emitting element 34J, a light-emitting element 34K, a light-emitting element 34L, a light-emitting element 34M, a light-emitting element 34N, a light-emitting element 34O, a fight-emitting element 34P, and a light-emitting element 34Q (FIG. 4) which are connected by conventional electrical wiring to a conventional electrical cable which threads from the interior of the outside housing 18 to its exterior via a cable through hole 28 (FIG. 1). The conventional electrical cable is fixed in place within hole 28 by a cable retaining screw 38 (FIG. 1) and by a cable retaining screw 38A which are accessed from the end of a cable retaining screw relief cut 32 (FIG. 1) and a cable retaining screw relief cut 32A.

Materials: outside housing 18, inside housing 10, focus adjustment ring 20, and mount outer ring 36 can all be manufactured from any suitable metal or plastic or a combination of any suitable metal or plastic.

PREFERRED EMODIMENT—OPERATION

Figure 3:
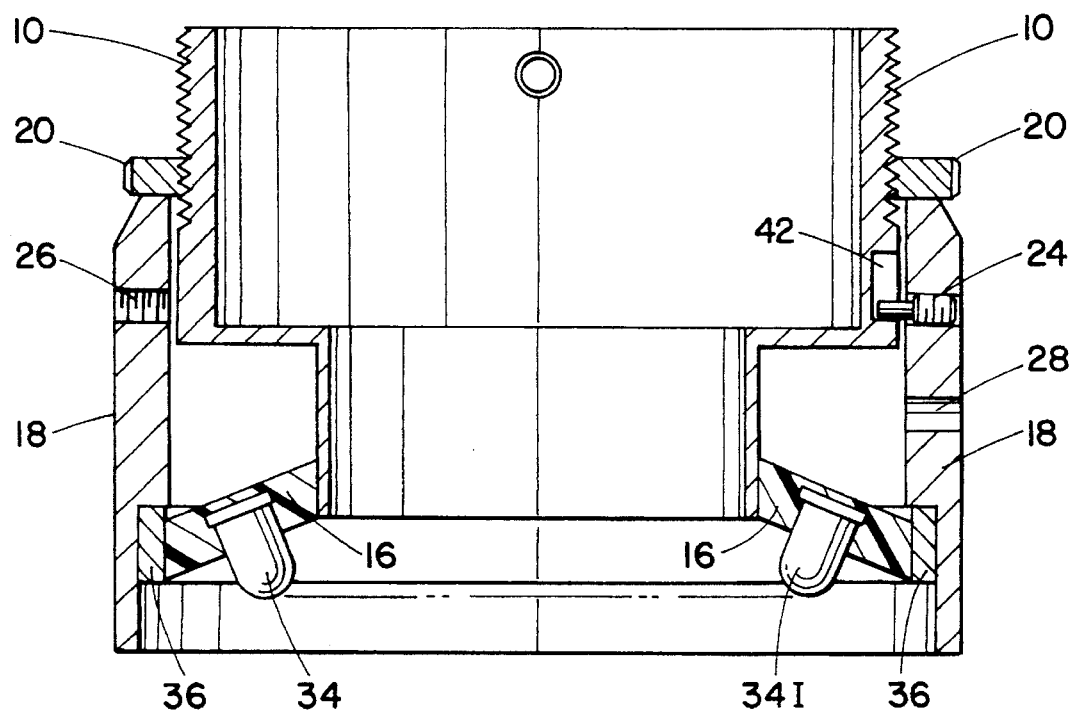
FIG. 3 shows a cross section of the invention with the flexible light-emitting element mount in the extreme flexed position.
Figure 5:
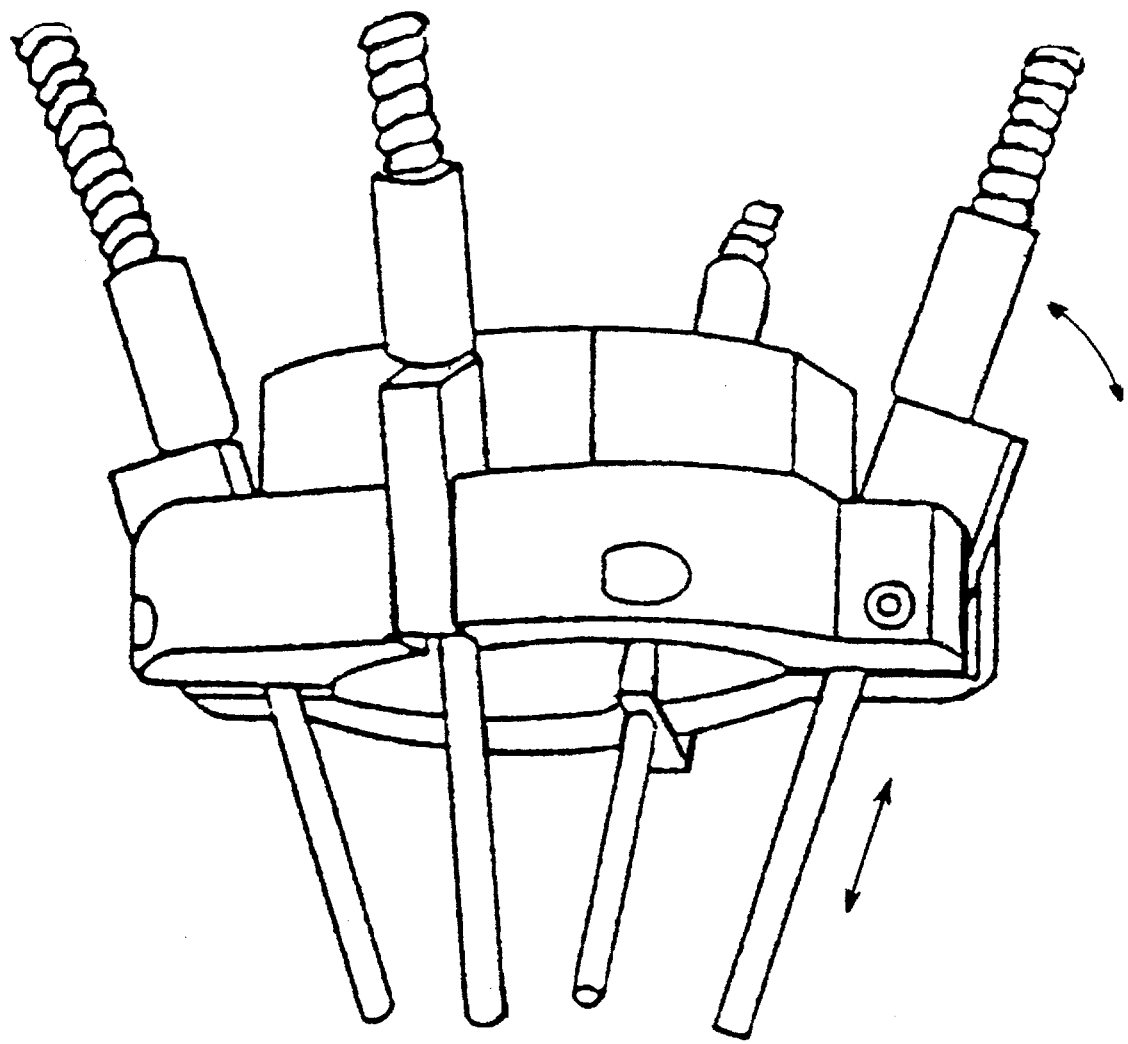
FIG. 5 shows an example of prior art- a device that holds four fiber optic cables.
Figure 6:
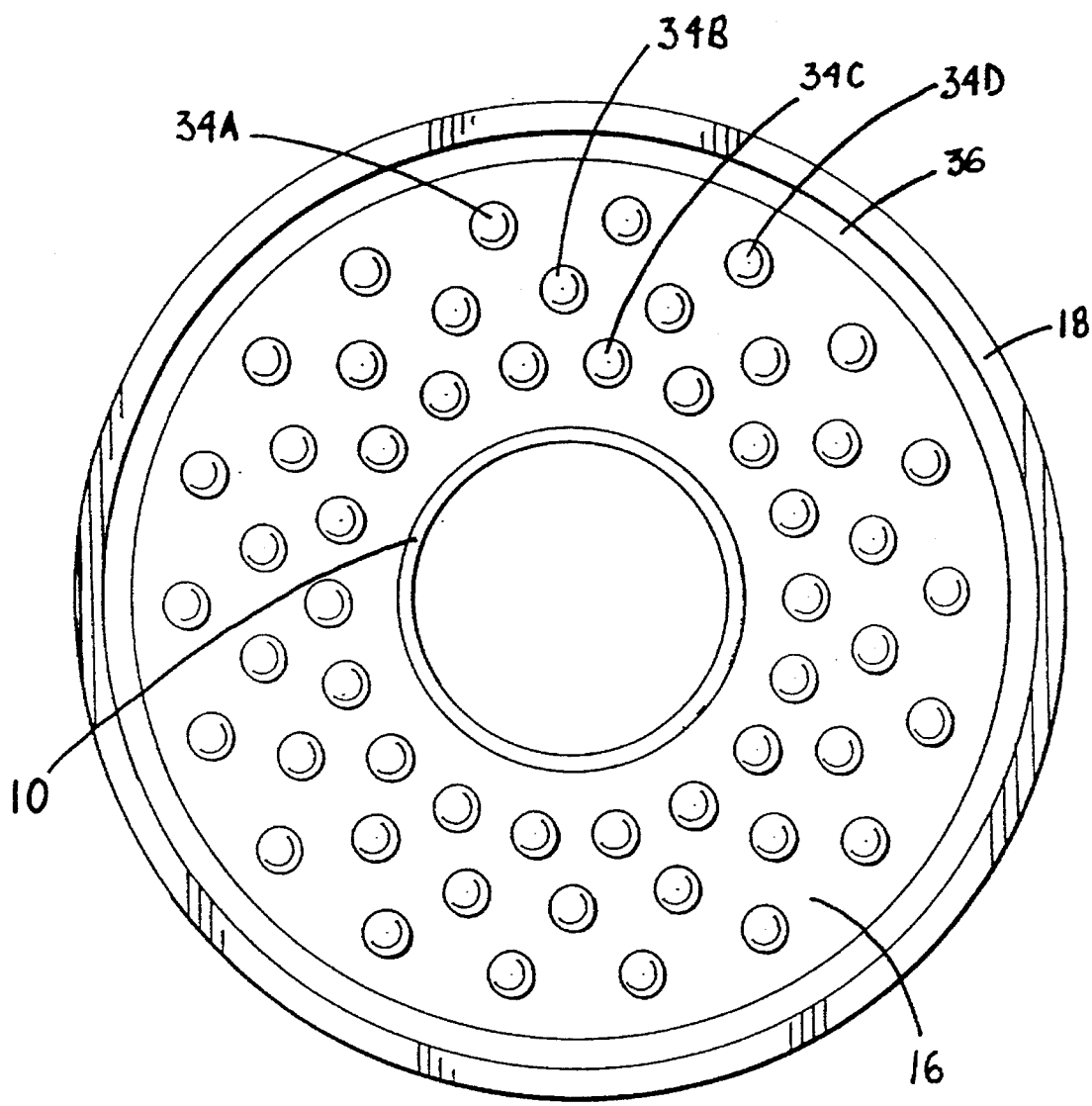
FIG. 6 is a view of the underside of an alternative embodiment having multiple rows of light-emitting elements.

Description of operation of embodiment as a unit:

When focus adjustment ring 20 (FIG. 2) is turned clockwise (looking down on the embodiment) this causes light-emitting elements 34–34Q to tip their lower end toward the center of the embodiment (FIG. 3). As ring 20 is turned elements 34–34Q continue to tip, their combined light output is focused at successively higher focal points. As ring 20 is turned counter-clockwise, elements 34–34Q tip their lower ends toward the outside of the embodiment resulting in successively lower focal points.

Description of operation of individual parts within embodiment:

As focus adjustment ring 20 (FIG. 2) is turned clockwise (looking down on the embodiment) it threads itself further down on inside housing 10. This causes a downward displacement of outside housing 18 with respect to inside housing 10 (see FIG. 3) which also causes a downward displacement of mount outer ring 36 and of the outside edge of flexible light-emitting element mount 16. This results in the subsequent angular displacement of the light-emitting elements 34–34Q. Focus adjustment limit screw 24 has an end which rides in focus adjustment limit slot 42. These components limit the degree of movement up or down and prevent the embodiment from being damaged through excessive displacement. Focus adjustment lock screw 26 binds inside housing 10 to outside housing 18 preventing changes in relative displacement. This prevents the focal length from accidentally shifting once the embodiment has been optimized for a given application. The embodiment may be attached to another device (television camera, microscope, etc.) by using mounting screw 22, mounting screw 22A and mounting screw 22B. As has been mentioned above, one molded flexible light-emitting element mount 16 controls the angles of all 18 light-emitting elements 34–34Q that are attached to it. This is an extreme reduction in complexity and cost when compared to those systems that use separate means to control each of their light-emitting elements.

Conclusions, Ramifications, and Scope

Accordingly, it can be seen that the focusing flexible mount of the invention provides a highly reliable yet simple and economical method of focusing multiple light-emitting elements that is convenient to use.

Although the description above contains many specificities, these should not be construed as limiting the scope of the invention but as merely providing illustrations of some of the presently preferred embodiments of this invention. Various other embodiments and ramifications are possible within it's scope. For example, the focusing flexible mount 16 could be made to focus a lesser or greater number of light-emitting elements than the preferred embodiment. The focusing flexible mount 16 could be made to focus multiple rows of light-emitting elements. Remote or electronic means could replace the focus adjustment ring 20. The focusing flexible mount 16 could be made to focus multiple lasers into a spot over a wide range of working distances. A flexible circuit board could replace the flexible plastic used in the flexible mount 16. Instead of using the flexible mount to hold the light-emitting element, it could hold a socket which would hold the light-emitting element 34. An alternate construction involves affixing the light-emitting elements to the flexible mount by screws, rivets, etc. instead of molding the elements directly into the flexible mount. A device could be made to focus individual light-emitting elements of varying colors/frequencies to achieve an illuminating effect that sums the individual elements colors (example: red light emitting diodes and white incandescent bulbs could be alternated along the mount to produce an illuminating effect that appears pink and yet is adjustable over a wide range of working distances.)

Thus the scope of the invention should be determined by the appended claims and their legal equivalents, rather than by the examples given.

What is claimed is:

1. A focusing light source for use with a viewing device such as a camera, comprising:

a flexible membrane;

a viewing opening generally centered in the membrane;

a plurality of light emitting elements attached to the flexible membrane; and, means of flexing said membrane in a predetermined manner, whereby causing said light emitting elements to have their collective outputs focused at a common area that is relational to the degree of flex in said membrane.

2. The focusing light source of claim 1 wherein the means of flexing is spaced from the generally centered viewing opening.

3. The focusing light source of claim 1 wherein said plurality of light emitting elements are at least partially molded into said flexible membrane.

4. The focusing light source of claim 1 wherein said means of flexing comprises said membrane having an inside portion that is axially adjustable in relation to an outside portion of said membrane along a central axis defined by the flexible membrane.

5. The focusing light source of claim 4 wherein said flexible membrane is interconnected between an inside housing and an outer ring.

6. The focusing light source of claim 5 wherein said outer ring is securable in a shoulder on the inside of an outer housing.

7. The focusing light source in claim 1 further comprising an outer housing and an inner housing whereby the flexible membrane extends between the outer and inner housings and houses the plurality of light emitting elements.

8. The focusing light source in claim 1 wherein the light emitting elements are each light emitting diodes that are evenly spaced around a central axis defined by the membrane.

9. The focusing light source in claim 1 wherein the light emitting elements are each light emitting diodes that are arranged in multiple rows in the ring-shaped membrane.

10. The focusing light source in claim 1 wherein the light emitting elements are each light emitting diodes that are equidistant from a central axis defined in the viewing opening within the membrane.

11. The focusing light source of claim 1 wherein said flexible membrane is interconnected between an inside housing and an outer ring which is securable in a shoulder on the inside of an outer housing.

12. The focusing light source of claim 11 wherein said means of flexing said membrane comprises a focus adjustment ring that forces the inside housing to move in relation to the outside housing thereby flexing said membrane.

13. The focusing light source of claim 12 further comprising a focus adjustment limiter for restricting the movement of the inside housing in relation to the outside housing to a preselected parameter.

14. The focusing light source of claim 12 further comprising a focus adjustment lock for locking the inside housing relative to the outside housing for selectively prohibiting relative displacement in between desired adjusting.

15. A focusing light source, comprising:

an inside housing having a first open passageway therein;

an outside housing having a second open passageway therein aligned with the first open passageway thereby defining an aperture through the focusing light source;

a plurality of light emitting elements dispersed around the aperture and focusable along an axis passing through the aperture; and, means for simultaneously adjusting the direction of the light output from all of the plurality of light emitting elements in a manner continually converging the light output of each of the plurality of light emitting elements together at a collective focal point as the collective focal point is adjusted along the axis to a desired focal point.

16. The focusing light source in claim 15 wherein said means for simultaneously adjusting further includes a flexible membrane affixed between the housings, adjustably holding the plurality of light emitting elements, and having the aperture centered therein.

17. The focusing light source in claim 16 wherein said means for simultaneously adjusting further includes a focus adjustment ring that forces the inside housing to move in relation to the outside housing.

18. The focusing light source in claim 16 wherein the light emitting elements are each light emitting diodes that are evenly spaced in the flexible membrane and are arranged in multiple rows around the axis passing through the aperture.

19. The focusing light source in claim 16 wherein the light emitting elements are each light emitting diodes that are evenly spaced in the flexible membrane and equidistant from the axis passing through the aperture.

20. A method of simultaneously adjusting a plurality of light emitting elements housed in a flexible membrane to focus the plurality of light emitting elements at a desired focal point after each movement of the desired focal point while simultaneously viewing any specimens located at the desired focal area using a viewing device such as a camera, comprising:

aligning a viewing device within an aperture in a flexible membrane housing a plurality of light emitting elements and affixed between a pair of axially adjustable housings;

altering the location of a desired focal area; and simultaneously adjusting the direction of the light output from all of the plurality of light emitting elements in a manner continually converging the light output of each of the plurality of light emitting elements together at a collective focal area as the collective focal area is adjusted to the desired focal area.

* * * * *